(12) United States Patent
Hornegger

(10) Patent No.: US 7,077,568 B2
(45) Date of Patent: Jul. 18, 2006

(54) X-RAY EXAMINATION METHOD AND APPARATUS WITH AUTOMATIC GATING OF THE X-RAY BEAM

(75) Inventor: Joachim Hornegger, Möhrendorf (DE)

(73) Assignee: Siemens Aktiengesellschaft, Munich (DE)

( * ) Notice: Subject to any disclaimer, the term of this patent is extended or adjusted under 35 U.S.C. 154(b) by 47 days.

(21) Appl. No.: 10/870,238

(22) Filed: Jun. 17, 2004

(65) Prior Publication Data

US 2005/0013410 A1  Jan. 20, 2005

(30) Foreign Application Priority Data

Jun. 17, 2003  (DE) .............. 103 27 293.3

(51) Int. Cl.
*A61B 6/08* (2006.01)

(52) U.S. Cl. .................... 378/206; 378/205

(58) Field of Classification Search ............. 378/206, 378/205
See application file for complete search history.

(56) References Cited

U.S. PATENT DOCUMENTS

| 5,684,854 | A | * | 11/1997 | Hughes ............ 378/206 |
| 5,844,962 | A | * | 12/1998 | Kunert ............ 378/150 |
| 6,267,503 | B1 | * | 7/2001 | McBride .......... 378/206 |
| 6,502,984 | B1 | * | 1/2003 | Ogura et al. ....... 378/206 |
| 2002/0114426 | A1 | * | 8/2002 | Polkus et al. ...... 378/206 |

* cited by examiner

*Primary Examiner*—Edward J. Glick
*Assistant Examiner*—Krystyna Suchecki
(74) *Attorney, Agent, or Firm*—Schiff Hardin LLP

(57) ABSTRACT

An x-ray apparatus has an exposure unit with an x-ray radiator and a diaphragm in front thereof, and a camera system with which an adjustment image is acquired of a subject positioned in front of an x-ray exposure plane. Using the adjustment image, a region to be examined of the subject is identified and an area of the x-ray exposure plane is selected such that the projection of the region to be examined of the subject is substantially inscribed in the projection of the areal section. The diaphragm is adjusted such that the x-ray radiation generated by the x-ray radiator is incident on the x-ray exposure plane only within the selected areal section.

13 Claims, 3 Drawing Sheets

X-RAY EXAMINATION METHOD AND APPARATUS WITH AUTOMATIC GATING OF THE X-RAY BEAM

BACKGROUND OF THE INVENTION

1. Field of the Invention

The present invention concerns an x-ray examination method as well as an x-ray apparatus to implement the method.

2. Description of the Prior Art

Particularly in medical technology) imaging examination methods based on the acquisition of x-ray Images have increased for years. In general, the x-rays generated by an x-ray radiator are emitted in the direction of an x-ray exposure plane in which the x-ray radiation is detected. Classically, photographic x-ray films are used for detection of the x-ray radiation. More recently digital x-ray detectors also have been used as an alternative.

For the acquisition of the x-ray image, a subject to be examined, which for medical purposes normally is a body part of a patient, is positioned in the beam path of the x-ray radiation in front of the x-ray exposure plane. The image contrast results due to the spatially different strong attenuation of the x-rays penetrating the subject.

In order to reduce the radiation exposure of the patient during the x-ray acquisition a diaphragm is typically arranged in front of the x-ray radiator that gates an x-ray beam of a predetermined size from the total generated x-ray radiation. This ray beam is adjusted such that only the region of the subject to be examined, and a surface portion of the x-ray exposure plane behind this region is exposed with x-ray radiation. In contrast, the remaining spatial region is shadowed by the diaphragm from the x-ray radiation.

A conventional diaphragm has a number of diaphragm plates or lamellae that can be manually adjusted to set the size of the beam and thus the area to be exposed. In order to ease the adjustment of the diaphragm, the x-ray apparatus frequently is equipped with an optical adjustment aid, with a visible light source being operated in parallel with the x-ray radiator. The diaphragm is illuminated by this light source from behind (meaning in the propagation direction of the x-ray radiation) with visible light, so the light- and radiation-permeable diaphragm section of the diaphragm is projected in the x-ray exposure plane. The area to be exposed in the x-ray acquisition is thus visible as an illuminated area in the x-ray exposure plane. According to conventional technology, the plates of the diaphragm are now adjusted manually until the exposure area is congruent with the region of the subject to be examined, in particular with the body part of the patient to be examined.

The adjustment process, which is subsequently also designated as a "collimation", is relatively time-consuming. This is disadvantageous insofar as the patient must remain substantially motionless during the gating and the subsequent exposure.

It is accordingly desirable to an x-ray examination method to enable a particularly rapid collimation, but the border of the area to be exposed should enclose the region to be examined as exactly as possible in order to reduce the radiation exposure to the largest possible extent. Using conventional technology, these requirements run counter to one another, particularly because manual adjustment of the collimator normally becomes increasingly more time-consuming the more precisely the area to be exposed is matched to the region to be examined.

SUMMARY OF THE INVENTION

An object of the present invention is to provide an improved x-ray examination method of the type described above, as well as an x-ray apparatus particularly suited to implement the improved method.

The above object is achieved in accordance with the present invention by an x-ray examination method (using a camera system, and adjustment image of an examination subject, positioned in front of an x-ray exposure plane, Is acquired before obtaining an x-ray image of the subject. Using the adjustment images a region to be examined of the subject is automatically electronically identified and an area of the exposure plane is selected so that the projection of the region to be examined is substantially inscribed in the projection of the area in the image plane. A diaphragm disposed in front of the x-ray source is automatically electronically adjusted so that the x-ray radiation (x-ray beam) generated by the x-ray radiator is incident on the x-ray exposure plane only within the selected area.

The x-ray apparatus for implementing the method has an exposure unit with an x-ray radiator and diaphragm arranged in front of it. The exposure unit serves to expose a predeterminable area of an x-ray exposure plane with x-ray radiation. Before acquisition of the x-ray image, an adjustment image of a subject positioned in front of the x-ray exposure plane is acquired by a camera system. This is supplied in the form of image data to an evaluation unit that adjusts a diaphragm using the adjustment image. For this purpose, a region of the subject to be examined is automatically electronically identified on the adjustment image. After this region is determined, using the adjustment image an area of the x-ray exposure is selected according to the requirement that the projection of the region to be examined on the adjustment image is substantially inscribed in the projection of the selected area. The selected area is irradiated by the evaluation unit automatically adjusting the diaphragm such that the x-ray radiation generated by the x-ray radiator is incident only within the selected area on the x-ray exposure plane.

The selection of the area to be exposed ensues essentially automatically via the evaluation unit. This automation is particularly facilitated because the area is not determined using the actual x-ray apparatus, but instead is determined virtually using the acquired adjustment image. As a result of the automation, the collimation ensues extremely quickly, meaning without noticeable time loss. The x-ray acquisition therefore can be started as soon as the subject to be examined is positioned. Furthermore, a particularly precise setting of the area techniques, rather than by the inspection of a technician. The radiation exposure for the patient thus can be kept particularly low.

As described above, the area of the x-ray exposure plane to be exposed is selected so that the projection of the region of the subject to be examined on the adjustment image is "inscribed" in the projection of the area section. This means, in the mathematical sense, that—in the projection mapped to the adjustment image—the selected area section is selected sufficiently small that its side edges are directly tangent to the region to be examined. The context of the invention, however, the term "inscribe" means that the selected areas section also can be selected larger, by a less symmetrical or asymmetrical side distance, than the region of the subject to be examined. This can meaningful, for example, be to prevent a part of the region to be examined from "wandering out" of the x-ray image given a small movement of the patient. Solely for display-related reasons, it can also be desirable to select the area somewhat larger than the region to be examined.

In a preferred embodiment of the method, the region of the subject to be examined is demarcated by at least one visual marking before the acquisition of the adjustment image. The term "visual marking before the acquisition of the adjustment image. The term visual marking" means a marking that generates a contrast in the low-energy light range, and so is visible on the adjustment image. The visual marking preferable is not radio-opaque. This means that it allows x-ray to pass through it substantially unattenuated and so it is not visible in the x-ray image. In particular a colored tape or ribbon is used as a visual marking. Alternatively, the marking can ensue by a color drawn on the subject by the clothing covering the body region of a patient that is not to be examined.

The adjustment image is an image of the subject to be examined generated under the conventional lighting circumstances at the examination location. In contrast to the x-ray image the adjustment image is generated not by high-energy (penetrating) x-ray radiation but rather by low-energy electromagnetic radiation such as, for example, visible light or infrared light.

Thus, the use of a conventional digital color image camera is particularly suitable and cost-effective for the acquisition of the adjustment image. The identification of the region to be examined preferable ensue according to the rule that a contiguous color surface, completely outwardly demarcated, is detected by the adjustment image and is associated with the region to be examined. This association appropriately ensues by the detected color surface exhibiting a color lying within a predetermined color range. For example, by specification of a color range characteristic for human skin, the x-ray apparatus can be operated so that it selectively detects a demarcated skin area as the region to be examined. Alternatively, a black-and-white camera can be used.

The method described above for identification of the region to be examined also functions in an alternative embodiment of the x-ray apparatus in which an infrared camera is used as the camera system. Such an infrared camera converts spatial regions with different temperature into differently colored areas of the adjustment image. By specification of a suitable color range, the x-ray apparatus can in turn be directed to identify a skin area as a region to be examined using its characteristic skin temperature.

The detection of the region to be examined also optionally ensues using means for electronic pattern recognition. The x-ray apparatus thus can automatically detect a specific body part to be examined, for example a hand, dependent on its characteristic shape.

A light source preferable is operated in parallel with the x-ray radiator in order to visualize the area section adjusted by the diaphragm for the technician. The open diaphragm region (meaning the region of the diaphragm permeable to visible light and x-ray radiation) is projected on the x-ray exposure plane by the visible light generated by the light source, so the technician can monitor in a simple manner whether the area to be exposed has been correctly set in the aforementioned automated procedure. In order to manually readjust the area as necessary, the x-ray apparatus preferable also allows for manual adjustment of the diaphragm. This can ensue by data input and output units connected to the evaluation unit, such as a monitor, keyboard, mouse, etc., and operating software integrated into the evaluation unit.

If a number of modifications of the area are selectable in which the region of the subject to be examined is identically inscribed, the area thereby optimized in the course of the selection process, to the effect that its surface content is minimal. This surface minimization, which serves to reduce the radiation exposure, preferably is implemented with a mathematical minimization technique.

The diaphragm and (adapted thereto) the evaluation unit preferably operate such that the area exhibits a polygonal, in particular rectangular, shape so the side edges, meaning the straight line segments between the corners of the polygon, can be moved independently of one another. For improved area optimization of the area the diaphragm and the evaluation unit can operate to allow the area to be rotated around the defined axis by the radiation propagation direction.

DESCRIPTION OF THE PREFERRED EMBODIMENTS

Figure 1:
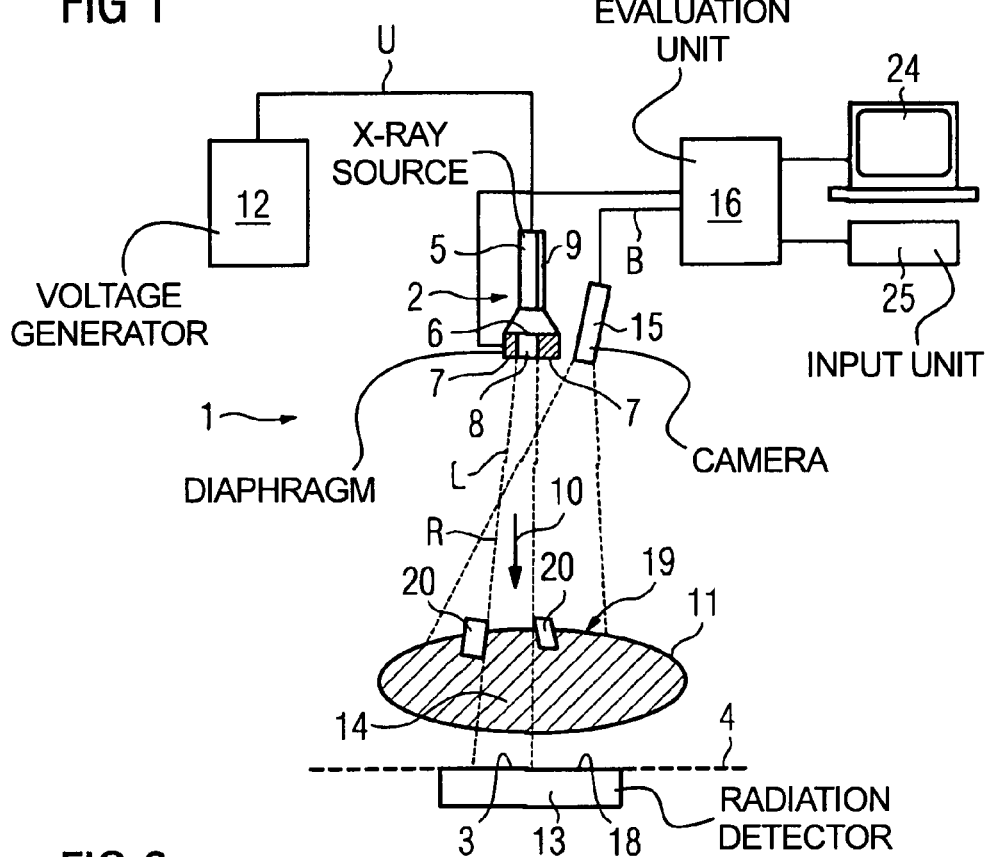
FIG. 1 schematically illustrates an x-ray apparatus in accordance with the invention with an exposure unit formed from an x-ray radiator and a collimator in front of said x-ray radiator, to expose a predeterminable area of an x-ray exposure plane with x-rays; with a camera system for acquisition of an adjustment image; and with an evaluation unit for evaluation of the adjustment image and for automatic adjustment of the collimator.

The x-ray apparatus 1 shows in FIG. 1 has an exposure unit 2, by means of which a predeterminable area 3 of an x-ray exposure plane 4 can be exposed with x-ray radiation R.

The exposure unit 2 includes an x-ray radiator 5 to generate the x-ray radiation R as well as a diaphragm 6. The term "diaphragm" In radiology means a device that includes a material (for example, lead) that significantly absorbs x-ray radiation R and that serves to gate or focus beams as well as to shield from scattered radiation (see, for example, "Psychrembel Klinisches Wöterbuch", 259th new edited edition. Berlin: De Gruyter, 2002, P. 879). The diaphragm 6 according to FIG. 1 has a number of adjustable plates or lamellae 7 that delimit a radiation-permeable region 8. The x-ray radiation R penetrating through this region 8 is incident within the area 3 on the x-ray exposure plane 4. In contrast, the region of the x-ray exposure plane 4 lying outside of the area 3 is shadowed from the x-ray radiation R by the radiation-impermeable plates 7.

To visualize the area 3, a light source 9 that emits visible light L in the propagation direction 10 of the x-ray radiation R is operated in parallel with the x-ray radiator 5. This light L illuminates the collimator 6 from behind (viewed form the x-ray exposure plane 4) and thus projects the region 8 on the x-ray exposure plane 4. The area 3 to be exposed thus appears as an illuminated area on the x-ray exposure lane 4, insofar as it is not shadowed by light-impermeable material.

For the x-ray examination, a subject 11 to be examined is positioned In front of the x-ray exposure plane 4 (viewed in the propagation direction 10) in the beam path of the x-ray radiation R. For x-ray acquisition, the x-ray radiator 5 is energized with a supply voltage U from an x-ray generator 12. The x-ray radiation R that is generated penetrates the object 11 with varying intensity (dependent on the spatial absorption cross-section of the subject 11) and is detected in a spatially resolved manner by an x-ray detector 13 disposed in the x-ray exposure plane 4. The x-ray detector 13 can be a conventional photographic x-ray film or a digital x-ray detector.

For the medical applications, the subject 11 to be examined normally is a body part of a patient. In order to reduce as much as possible the exposure of the patient by the hard x-ray radiation R, it is particularly important to limit the area 3 to be exposed as precisely as possible to the region 14 to be examined of the subject 11. In the x-ray apparatus 1, this adjustment of the area 3 to be exposed ensues automatically. For this purpose, the x-ray apparatus 1 has a camera system 15. This camera system 15 is a conventional digital color image camera or a digital infrared camera. The camera system 15 is aligned substantially parallel to the exposure unit 2 and acquires an adjustment image B of the x-ray exposure plane 4 and of the subject 11 positioned thereon and transmits this image B to an evaluation unit 16 in the form of digital image data. The evaluation unit 16 preferably is a data processing system equipped with suitable image-processing software. The evaluation unit 16 operates as subsequently explained in detail, to identify the region 14 to be examined of the subject 11, to (using the adjustment image B) the area (set) 3 to the region 14 to be examined, and to correspondingly adjust the diaphragm 6 such that only the adapted area 3 is exposed with x-ray radiation R.

Figure 2:
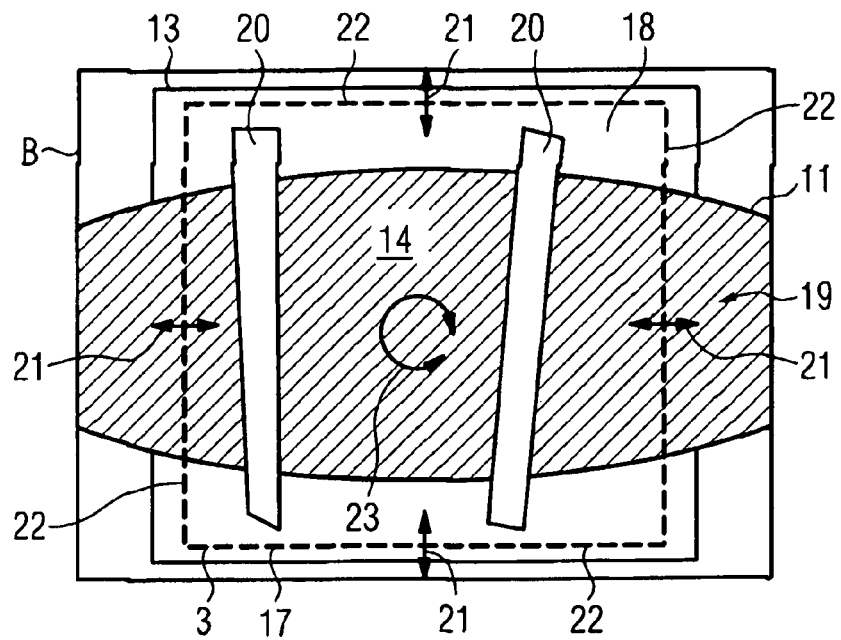
FIG. 2 schematically shows an adjustment image of the x-ray exposure plane a subject positioned in front of the x-ray exposure plane, before adaptation of the area in accordance with the invention.

To explain the method implemented by the evaluation unit 16, schematically shown in FIG. 2 is an adjustment image B acquired by the camera system 15, in which the projection of the subject 11 can be recognized in front of the projection of the x-ray detector 13. Furthermore, in the schematic adjustment image B, a frame 17 that corresponds to the projection of the exposable areal section 3 is shown with a dashed line.

The adjustment image B is acquired before the x-ray image. The frame 17, and with it the border of the area 3, is in this stage of the x-ray acquisition event set substantially larger than the region 14 of the subject 11 to be examined, the projection of which in FIG. 2 is disposed somewhat centrically relative to the adjustment image B. Rather, according to FIG. 2, the area 3 almost completely covers the detection area 18 of the x-ray detector 13.

In order to enable automatic collimation, the region 14 of the subject 11 to be examined is initially marked by a technician, at least on the side 19 of the subject 11 facing the camera system 15. For marking, two colored material bands or ribbons 20 are used that are attached to the subject 11 at a spacing from one another, such that the projection of the region 14 to be examined on the adjustment image B is framed on both sides by the projections of both material bands 20. The projection of the region 14 to be examined thus forms a contiguous color area, completely outwardly delimited, that is detected by the evaluation unit 16 using known electronic image processing techniques and is associated with the region 14 to be examined.

The evaluation unit 16 now reduces the size of the frame 17 until the projection of the region 14 to be examined is inscribed In the frame 17. For this, the evaluation unit can (as is indicated by the arrow 21 in FIG. 2) move each of the four side edges 22 of the rectangular frame 17 independently of one another and transversely to the respective extent of the side edge 22. The frame 17 furthermore (as indicated by the arrow 23) can be rotated in the image plane of the adjustment image B.

Figure 3:
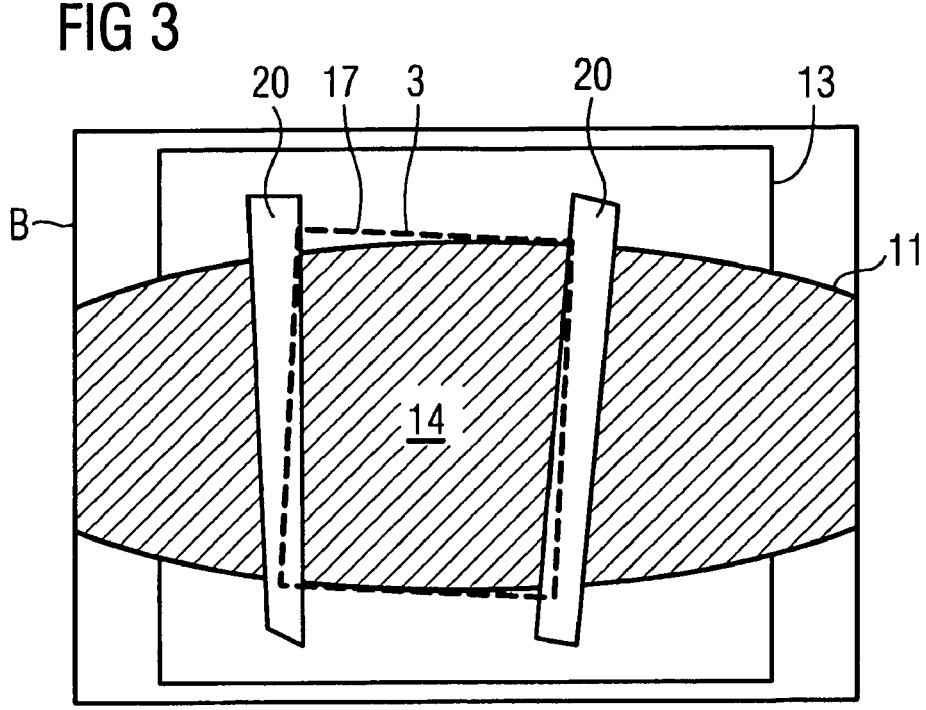
FIG. 3 shows the adjustment image according to FIG. 2 after adaptation of the area section.

With the degrees of freedom given by the arrows 22 and 23, substantially arbitrary modifications of the frame 17 can in principle be generated in which the projection of the region 14 to be examined is inscribed exactly. Among these modifications of the frame 17, the evaluation unit 16 selects, using a mathematical minimization method, that modification of the frame 17 with the smallest area content. FIG. 3 again shows the adjustment image B according to the FIG. 2, but with frame 17 optimized with regard to its area content in which the region 14 of the subject 11 to be examined is inscribed.

The diaphragm 6 of the x-ray apparatus 1 is adjustable such that the area 3 also can be modified corresponding to the arrows 21 and 23. After the evaluation unit 16 has implemented the optimization of the frame 17, it controls the diaphragm 6 so that the area 3 to be exposed is adapted to the border 17. After the end of the collimation event, the diaphragm 6 is thus adjusted such that only the area 3 (corresponding to the frame 17) of the x-ray exposure plane 4 is exposed with x-ray radiation R.

Figure 4:
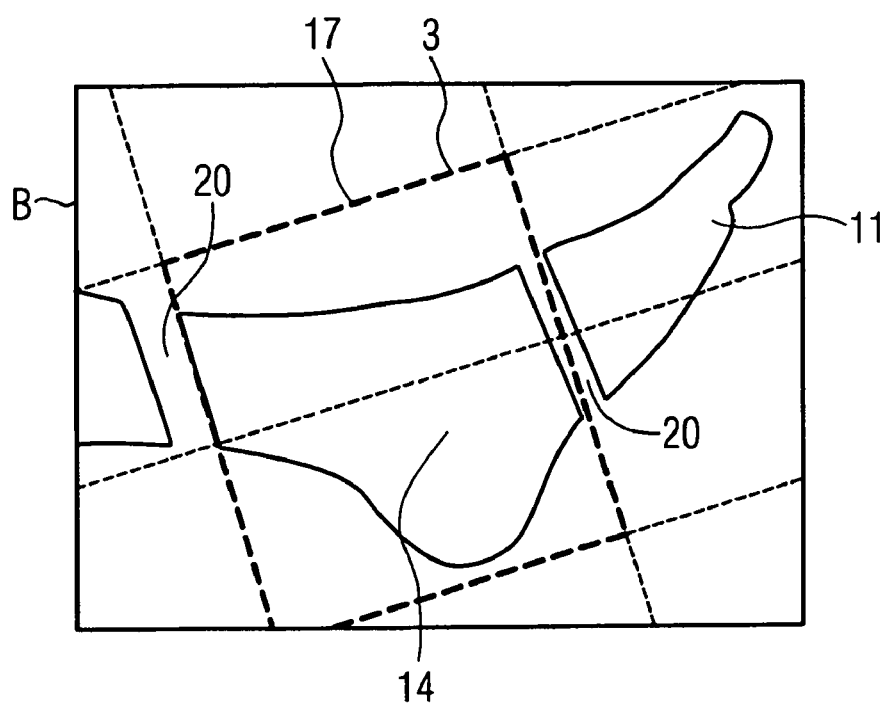
FIG. 4 shows an exemplary adjustment image according to FIG. 2, in which the subject is the foot of a patient.

In FIG. 4, a reality-approximating example of an adjustment image B is shown in which the subject 11 is the foot of a patient. The region 14 to be examined, that in this case is the ankle of the foot, is marked on both sides by colored bands 20 the color of which somewhat corresponds to the color of the image background and which therefore is not emphasized by the image background. Analogous to the representation according to FIG. 3, in FIG. 4 a frame 17 adapted to the region 14 to be examined is mapped via dashed lines, said frame 17 corresponding to the areal section 3 to be exposed. As can be seen from the representation according to FIG. 4, the region 14 to be examined is not exactly inscribed in the frame 17 in the mathematical sense. Rather, the frame 17 is selected slightly larger than would be necessary for representation of the region 14 to be examined. This is primarily for presentation-related reasons. In particular, in this manner the ankle is approximately centered with regard to the middle of the frame 17, and therewith to the image center of the x-ray image to be acquired.

Figure 5:
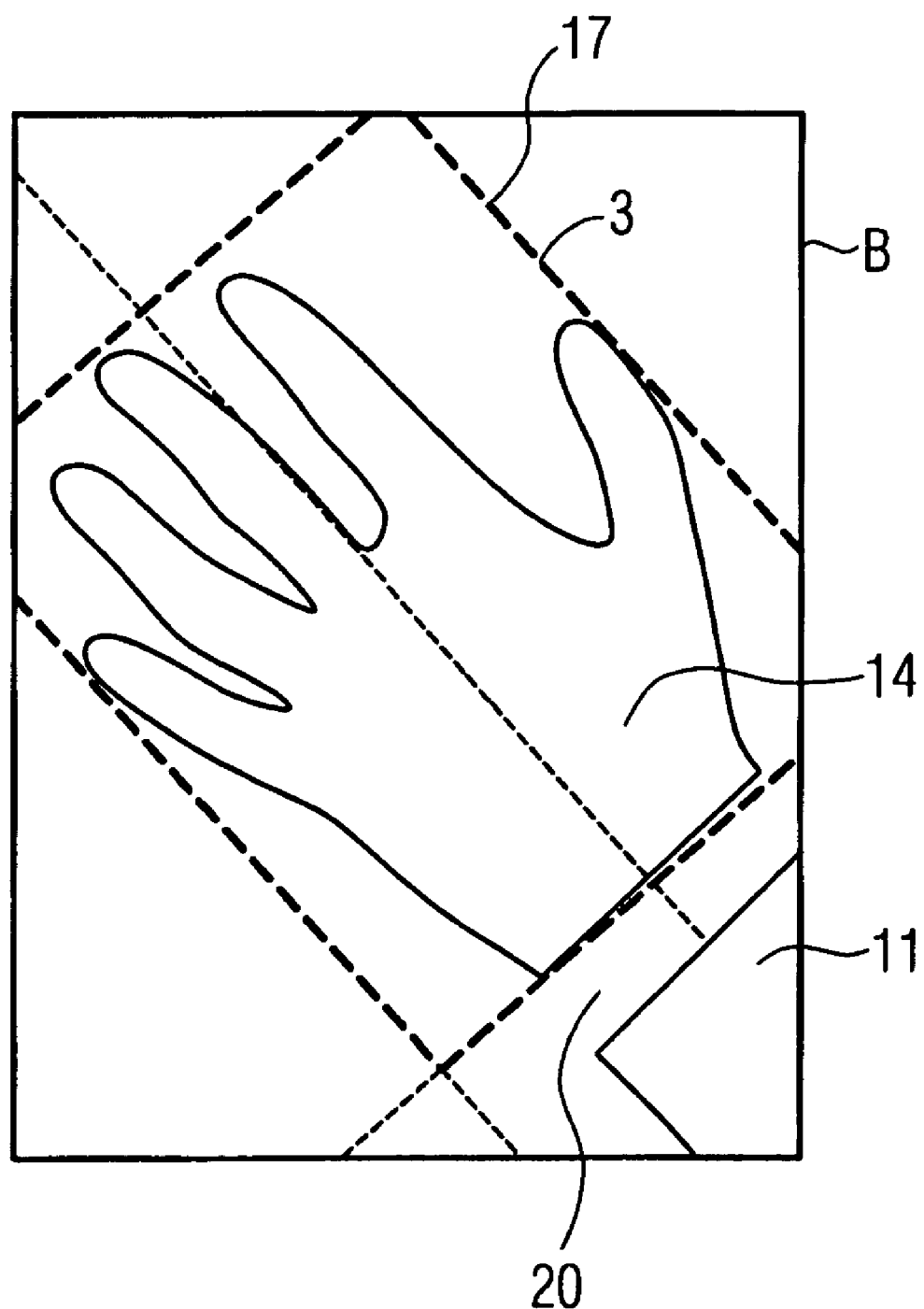
FIG. 5 shows a further exemplary adjustment image in which the subject is the hand of a patient.

In FIG. 5, a further reality-approximating example of an adjustment image B is shown. The subject 11 to be examined is here the arm of a patient. The region 14 to be examined of this arm is the hand of the patient. For marking in this case, a material band 20 looped around the wrist is sufficient, the band 20 likewise being adapted in terms of color to the image background and likewise for this reason not visibly emphasized by the image background. The projection of the hand is already sufficiently demarcated by the one material band 20 in order to form a closed color area, outwardly demarcated on all sides, that can be detected by the evaluation unit 16 as a region 14 to be examined. FIG. 5 furthermore shows a frame 17, adapted to this region 14 to be examined, that in turn corresponds to the areal section 3 to be exposed with x-ray radiation R, and in which the region 14 to be examined is inscribed.

In order to support the automatic recognition of the region 14 to be examined, at least one selection criterion is preferably predetermined for the evaluation unit 16. The evaluation unit thus preferably searches for color areas having a coloration that lies within a predetermined color range. This color range appropriately encompasses all occurring skin colors. The evaluation unit 16 is thus selectively directed to the detection of skin regions rather than to region 14 to be examined. By contrast, colors are preferably used for marking that prominently deviate from skin color, for example a fluorescent green or blue. Furthermore, the evaluation unit 16 preferably begins with the search for contiguous color areas in the middle of the adjustment Image B. It can thereby be excluded that peripheral color areas (such as, for example, the toe in FIG. 4 lying outside of the region 14 to be examined) are falsely associated with the region to be examined. The evaluation unit 16 is optionally furthermore equipped with means for automatic shape (pattern) recognition, such that the region 14 to be examined is already detected using the characteristic shape of the corresponding body part, for example the hand mapped in FIG. 5.

The apparatus 1 preferably allows the automatic collimation to be manually readjusted. The evaluation unit 16 thus is preferably equipped with data input and output units, in particular a screen 24 as well as a keyboard 25 or a mouse. Via the screen 24, the adjustment image B is displayed for the technician corresponding to the representation according to FIG. 2 through 5. The technician can manually change the area 3 as necessary, for example by changing the frame 17 with via the keyboard 25 or with the mouse. These changes are subsequently converted by the evaluation unit 16 into a change of the real area 3 by corresponding adjustment of the diaphragm 6. Using the area 3 optically illuminated by the light source 9, the technician can test at any time whether the collimation performed by the evaluation unit 16 according to the technician's intentions has been transferred to the real x-ray apparatus 1.

Although modifications and changes may be suggested by those skilled in the art, it is the intention of the inventor to embody within the patent warranted hereon all changes and modifications as reasonably and properly come within the scope of his contribution to the art.

I claim as my invention:

1. An x-ray examination method comprising:
   before irradiating an examination region of a subject with x-rays for obtaining an x-ray image of the region in an x-ray exposure plane disposed behind the subject, demarcating said examination region on said subject with at least one visual marking formed by a colored band applied on the subject and acquiring an adjustment image, encompassing the examination region and in which said colored band is detectable, with a camera operating with non-penetrating radiation;
   automatically electronically analyzing said adjustment image for identifying said examination region therein and selecting an area projected in said x-ray exposure plane wherein a projection of said examination region in said exposure plane is substantially inscribed; and
   irradiating said subject with x-rays with an x-ray source and automatically electronically adjusting a diaphragm disposed in a path of said x-rays for gating said x-rays for causing said x-rays to be incident in said x-ray exposure plane only within said selected area.

2. An x-ray examination method as claimed in claim 1 wherein the step of automatically identifying said examination region in said adjustment image comprises identifying, as said examination region, a demarcated, contiguous colored area in said adjustment image.

3. An x-ray examination method as claimed in claim 2 comprising identifying said color area as an area having a color within a predetermined range.

4. An x-ray examination method as claimed in claim 1 wherein the step of automatically electronically identifying said examination region in said adjustment image comprises analyzing said adjustment image using computerized pattern recognition.

5. An x-ray examination method as claimed in claim 1 wherein said diaphragm has an open region through which said x-rays pass substantially unattenuated, and comprising illuminating a projection of said diaphragm region on said examination subject with visible light.

6. An x-ray examination method as claimed in claim 1 comprising optimizing said selected area by minimizing an area content thereof.

7. An x-ray examination method as claimed in claim 1 comprising allowing subsequent manual adjustment of said diaphragm for manually adjusting said selected area that has been automatically electronically selected.

8. An x-ray apparatus comprising:
   an x-ray radiator that emits x-rays;
   a diaphragm disposed in a path of said x-rays for gating said x-rays;
   a radiation detector having an x-ray exposure plane for detecting x-rays to generate an image of an examination region of a subject disposed between said x-ray source and said x-ray exposure plane;
   a colored band, adapted to be applied to the subject, that demarcates said examination region:
   a camera, operating with non-penetrating radiation, for obtaining an adjustment image of the subject, in which said colored band is detectable, prior to irradiating subject with said x-rays; and
   an evaluation unit supplied with said acquisition image for automatically electronically detecting, in said adjustment image, the demarcated examination region of the subject and for selecting an area in said x-ray exposure plane wherein a projection of said examination region in said exposure plane is inscribed, and for automatically adjusting said diaphragm for gating said x-rays for causing said x-rays to be incident in said x-ray exposure plane only within the selected area.

9. An x-ray apparatus as claimed in claim 8 wherein said camera is a color image camera.

10. An x-ray apparatus as claimed in claim 8 wherein said camera is an infrared camera.

11. An x-ray apparatus as claimed in claim 8 wherein said diaphragm gates said x-rays to produce said area with a polygonal shape, having edges that are adjustable independently of each other by adjusting said diaphragm.

12. An x-ray apparatus as claimed in claim 8 wherein said x-rays propagate in a propagation direction, and wherein said diaphragm is adjustable to rotate said area around an axis defined by said propagation direction.

13. An x-ray apparatus as claimed in claim 8 wherein said diaphragm has a region through which said x-rays pass substantially unattenuated, and wherein said x-ray apparatus comprises a light source for emitting visible light passing through said region, for illuminating a projection of said region of said diaphragm on the subject.

* * * * *